United States Patent
Keene

(10) Patent No.: US 7,735,878 B2
(45) Date of Patent: Jun. 15, 2010

(54) SELF-SETTING HIGH PRESSURE FITTING

(75) Inventor: Russell Keene, Sudbury, MA (US)

(73) Assignee: Waters Technologies Corporation, Milford, MA (US)

( * ) Notice: Subject to any disclaimer, the term of this patent is extended or adjusted under 35 U.S.C. 154(b) by 210 days.

(21) Appl. No.: 10/597,829

(22) PCT Filed: Mar. 2, 2005

(86) PCT No.: PCT/US2005/006755

§ 371 (c)(1),
(2), (4) Date: Aug. 9, 2006

(87) PCT Pub. No.: WO2005/084337

PCT Pub. Date: Sep. 15, 2005

(65) Prior Publication Data

US 2007/0158942 A1    Jul. 12, 2007

Related U.S. Application Data

(60) Provisional application No. 60/549,183, filed on Mar. 2, 2004.

(51) Int. Cl.
*F16L 25/00* (2006.01)
(52) U.S. Cl. .................... 285/332; 285/342
(58) Field of Classification Search ............... 285/332, 285/9.2, 342, 343
See application file for complete search history.

(56) References Cited

U.S. PATENT DOCUMENTS

| | | | |
|---|---|---|---|
| 2,208,292 A | 7/1940 | Hanson et al | |
| 3,067,777 A | * 12/1962 | Briscoe | ......... 138/44 |
| 3,973,792 A | 8/1976 | Gonner et al. | |
| 4,084,843 A | 4/1978 | Gassert | |
| 4,121,859 A | 10/1978 | DeMey, II | |
| 4,230,349 A | 10/1980 | Normark | |
| 4,669,756 A | 6/1987 | Cassaday | |
| 4,679,824 A | 7/1987 | Rodriguez et al. | |
| 4,991,883 A | 2/1991 | Worden | |
| 5,163,722 A | 11/1992 | Worden | |
| 5,234,235 A | 8/1993 | Worden | |
| 5,344,195 A | 9/1994 | Parimore, Jr. et al. | |
| 5,601,785 A | 2/1997 | Higdon | |

(Continued)

*Primary Examiner*—Aaron M Dunwoody
(74) *Attorney, Agent, or Firm*—Anthony J. Janiuk

(57) ABSTRACT

A coupling element (1) comprising a male sealing element (5) is disclosed herein. The male sealing element comprises a first end (7), second end (9), and a longitudinal axis extending between the first and second end. The coupling element is housed within a nut (3). In one aspect, the male sealing element has a generally cylindrical shape. Also, the male sealing element defines a fluid passageway therethrough for the transmission of fluid. The male sealing element is secured to a ferrule (13) which is located within a cavity of the nut. The first end of the male sealing element defines a conical sealing surface. In one aspect, the male conical sealing surface (17) mates with a female sealing element (23) which has a receptacle that is defined by a nearly complementary conical geometry. In this aspect, the male conical sealing surface has a mismatched angle when compared to the complementary conical female sealing element. The coupling element also has a biasing element (19) disposed between a retaining ring and the ferrule located within the nut cavity. This biasing element facilitates a fluid-tight, metal to metal (or metal to plastic, or plastic to plastic) seal between the male sealing element and female sealing element.

10 Claims, 3 Drawing Sheets

U.S. PATENT DOCUMENTS

| | | |
|---|---|---|
| 5,667,255 A | 9/1997 | Kato |
| 5,848,813 A | 12/1998 | Albrecht |
| 6,050,544 A | 4/2000 | Meronek |
| 6,102,449 A | 8/2000 | Welsh |
| 6,193,286 B1 | 2/2001 | Jones et al. |
| 6,585,296 B1 | 7/2003 | Picha |

* cited by examiner

US 7,735,878 B2

SELF-SETTING HIGH PRESSURE FITTING

CROSS REFERENCE RELATED APPLICATION INFORMATION

This application claims priority from the United States Provisional Patent Application No. 60/549,183, filed Mar. 2, 2004. The contents of these applications are incorporated herein by reference.

FIELD OF INVENTION

This invention relates generally to connectors for tube assemblies, and, more particularly, to a self-setting high pressure fitting for creating a high pressure seal.

BACKGROUND OF THE INVENTION

High pressure systems are routinely employed in analytical laboratories, for example, in the isolation and characterization of a particular compound. As the demand for high pressure systems continues, the demand for high pressure seals follows.

At present, compression ferrules are used fluid line connectors in high pressure systems such as high performance liquid chromatography. These compression ferrules are relatively small structures that cooperate with one or two-piece tube fittings. These devices require precise machining of detailed ports where two fluid lines connect together, or where the fluid lines interconnect to components such as fluid manifolds and valves. As the number of these fluid interconnections increase the consequential cost of machined parts and the cost of production tooling increases.

Depending on frequency of use, the high pressure systems can exert a tremendous amount of stress on the fluid connects. The seal that is formed at the connection site can begin to deteriorate due to this stress.

The present fittings comprise a conical ferrule and a compression nut which are proximate to the tube end. The mating part has a threaded and conical machined recess at the receiving port which cooperates with the tube end compression nut and ferrule to make a seal. As the compression nut is tightened into threads of the machined port it forces the ferrule forward. This forward motion presses the conical ferrule end against the conical recess which causes the front edge of the ferrule to reduce in size until it fits tightly around the tube. The seal is achieved by the compression deformation of the ferrule by the port cone and by the compression deformation of the ferrule against the tube outside surface. Modern chromatographic system pressures are becoming greater than the present fittings are designed to sustain. The greater deformations needed to achieve sealing results in reduced reliability of the seals.

When the present fittings are assembled they sometimes have a characteristic which is detrimental to the quality of the chromatographic separation. There can be a cavity left between the tip of the tube and the bottom of the port. This cavity will retain fluids and can cause an unwanted mixing of fluid species during chromatographic separation. Minimizing this cavity depends on the skill of the person who makes-up the fitting as the ferrule closes on the tube. If the tube is held tightly into the port as the compression nut is tightened against the ferrule, the tube will be pressed forward while the ferrule collapses against it in order to close the tip gap.

The present fittings, once set, often cannot be interchanged among various ports because of the dead volume issue. When the ferrule is compressed on the tube at the first assembly the distance from the ferrule to the tube tip is unique for that port. If the tube and fitting is removed and used in a different port there may be a space left at the tube tip. This can adversely impact the chromatography when the tube carries fluids which should not be mixed.

There are high pressure seal assemblies that attempt to mitigate the problems described above. For example, there is disclosed a high pressure tube seating assembly wherein the seal is formed at a contact interface between a spherical distal end portion of a tube and a receiving surface. It is believed that as greater axial force is applied, the spherical distal portion deforms to more closely approximate the geometry of the receiving surface. However, in actuality, as greater axial pressure is applied, the spherical distal portion deforms but does not deform in such as manner as to significantly compliment the receiving surface.

In modern chromatographic systems pressures are being increased and the internal fluid volumes are being reduced. Therefore the reliability and seal characteristics of present fittings are becoming problematic. The present fitting has two seal surfaces which are both relatively larger than the fluid path diameter they are sealing. Those seal surfaces are remote from the tube tip and port opening so there is opportunity for fluid "dead-volume". As the pressure is raised the compression nut force and resulting distortion of the ferrule and related parts becomes excessive. As the system internal fluid volume becomes smaller the fitting dead-volume and especially sensitivity to the assemblers skill become major impediments to chromatographic quality.

There exists a current to have a high pressure fitting assembly that upon axial pressure will deform in such a manner as to compliment the receiving element, thereby, forming a high pressure seal with optimum fluid integrity.

BRIEF SUMMARY OF THE INVENTION

The present invention relates to a coupling element that is capable of axial displacement for use in a high pressure seal. This coupling element upon axial compression forms a fluid-tight seal.

A coupling element comprising a male sealing element is disclosed herein. The male sealing element comprises a first end, second end, and a longitudinal axis extending between the first and second end. The coupling element is housed within a nut. In one aspect, the male sealing element has a generally cylindrical shape. Also, the male sealing element defines a fluid passageway therethrough for the transmission of fluid. The male sealing element is secured to a ferrule which is located within a cavity of the nut. The first end of the male sealing element defines a conical sealing surface. In one aspect, the male conical sealing surface mates with a female sealing element which has a receptacle that is defined by a nearly complementary conical geometry. In this aspect, the male conical sealing surface has a mismatched angle when compared to the complementary conical female sealing element. The coupling element also has a biasing element disposed between a retaining ring and the ferrule located within the nut cavity. This biasing element facilitates a fluid-tight, metal to metal (or metal to plastic, or plastic to plastic) seal between the male sealing element and female sealing element.

A method of forming a high pressure seal is disclosed herein. An axial compression force can be applied to the male sealing element of the present invention. This compression force will displace the male sealing element toward a female sealing element. In one aspect, the male sealing element has a first end which defines a conical sealing surface. In this aspect, the female sealing element has a receptacle that defines a complementary conical geometry. There is a mismatch angle between the male conical surface and the female sealing element in this aspect. Deformation of the males first end conical surface occurs as the axial compression force is applied, thereby effectuating a fluid-tight seal.

For a better understanding of the present invention, together with other and further objects thereof, reference is made to the accompanying drawings and detailed description and its scope will be pointed out in the appended claims.

DETAILED DESCRIPTION OF THE INVENTION

The present invention relates to a coupling element that is capable of axial displacement for use in a high pressure seal. This coupling element upon axial compression forms a fluid-tight seal.

The coupling element of the present invention makes a seal just outside the fluid path's outer diameter so that it is as small and tight as possible. This eliminates dead-volume and minimizes seal force. Since the seal force is provided by a preset spring deflection, the coupling element is not subject to make-up error or to variations in seal from port to port. Pre-set fitting force also eliminates distortion due to over tightening.

Figure 1:
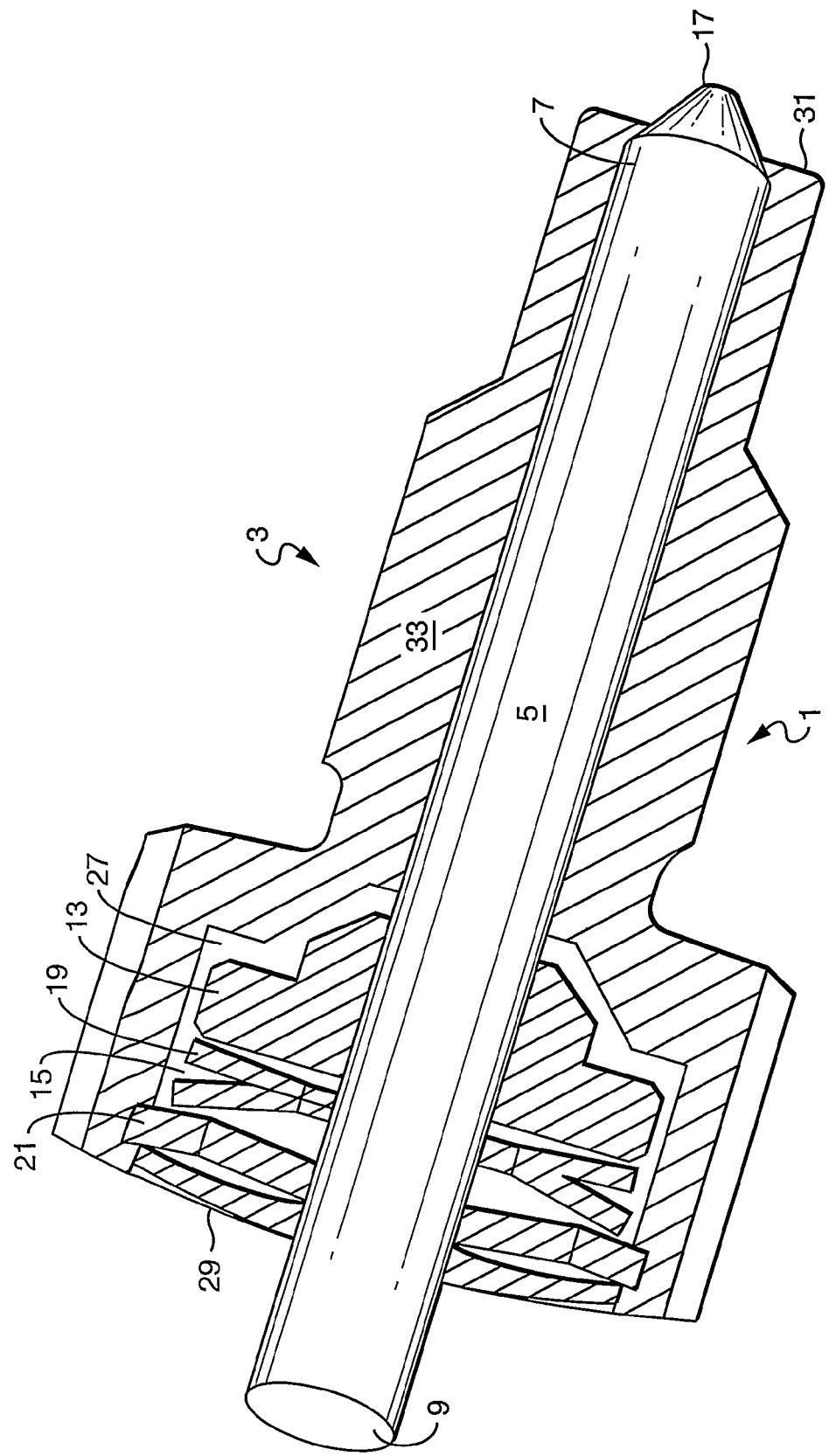
FIG. 1 is a schematic of one embodiment of the present invention.

A coupling element 1 comprising a male sealing element 5 is disclosed herein. See FIG. 1. The male sealing element 5 comprises a first end 7, second end 9, and a longitudinal axis extending between the first 7 and second end 9. The coupling element 5 is housed within a nut 3. In one aspect, the male sealing element 5 has a generally cylindrical shape. Also, the male sealing element 5 defines a fluid passageway therethrough for the transmission of fluid. The male sealing element 5 is secured in a ferrule 13 which is located within a cavity 15 of the distal portion of the nut 3. The first end 7 of the male sealing element 5 defines a conical sealing surface 17. In one aspect, the conical sealing surface 17 extends or protrudes beyond the proximal portion of the nut housing 33. This extension is about 0.030" nominally. In another aspect, the male conical sealing surface 17 mates with a female sealing element 23 which has a receptacle 25 that is defined by a nearly complementary conical geometry. See FIG. 2a. In one aspect, the male conical sealing surface 17 has a mismatched angle when compared to the complementary conical female sealing element 23. The coupling element 1 also has a pair of biasing elements 19 disposed between a retaining ring 21 and the ferrule 13 located within the nut cavity 15. See FIG. 1. The biasing elements 19 facilitates a fluid-tight, metal to metal seal between the male sealing element 5 and female sealing element 23.

Materials suitable for the present invention include, but are not limited to, stainless steel, PEEK, polyphenelyne sulfide, ceramic, polyamide, polyolefins, and alike. There can be a combination of materials used in this invention. For example, the male element 5 can comprise stainless steel, while the female element 23 can comprise a polymeric material such as polyphenelyne sulfide. Of course, the reverse can be true as well.

In one embodiment, the coupling element 1 has a longitudinal axis ranging from about 0.5" to about 0.7". The longitudinal axis being defined herein as the distance from the tip of the apical surface 17 of the male element 5 to the distal termination of the nut housing 33. Typical diameters for the male sealing element range from about 0.031" to about 0.094". In one aspect, the proximal portion of the male element 5 tapers forming, for example, a conical surface whose diameter changes as the geometry defines a conical surface. Materials suitable for the male element 5 include, but are not limited to, stainless steel, PEEK, polyphenelyne sulfide, ceramic, polyamide, polyolefins, and alike. The apical tip of the male element 5 can have a material different the rest of the male element. For example, the male tip can have a coating that would enhance sealing such as Teflon film.

The nut 3 is defined by a nut housing 33. The nut housing 33 generally encompasses a portion of the male element 5. In one aspect, a portion of the external surface of the nut housing 33 is defined by threads, for example, 10/32 or M4 threads. The general surface geometry of the nut housing 33 can follow that which is in the prior art and well known to those skilled in the art. In one aspect, the length of from the distal surface 29 of the nut housing 33 to the proximal surface 31 of the nut housing 33 ranges from about 0.5" to about 0.7". The diameter of the nut 3 changes as the perspective changes from the distal surface 29 to the proximal surface 31. Generally, the diameter of the nut housing 33 is greater than the male element 5. In one aspect, the male element 5 has a diameter ranging from about 0.031" to about 0.094". The ratio of diameter between the conical tip 17 of the male element 5 with the remaining portion of the element 5 is about 4 to 1. Suitable materials for the nut housing 33 include, but are not limited to, stainless steel, PEEK, polyphenelyne sulfide, ceramic, polyamide, polyolefins, and alike.

The nut 3 also defines a cavity 15 toward the distal portion of the nut 3. Residing within the cavity 15 is a retaining ring 21, biasing element 19, and a ferrule 13. The retaining ring 21 assists in retaining the integrity of the other elements within the nut 3. It also provides a surface for the biasing element 19 to be biased against as axial force is being applied. In one aspect, this force is applied as the nut 3 is threaded into a receptacle, such as the female sealing element 23 depicted in FIG. 2. The retaining ring 21 is disposed circumferentially about the interior of the nut cavity 15. In one aspect, the retaining ring 21 is disposed within a groove defined by the nut housing 33. The retaining ring 21 can comprise stainless steel as well as other suitable materials.

The biasing element 19 is disposed adjacent to the retaining ring 21. In one aspect, the biasing element 19 comprises a compression spring. In a particular aspect, the biasing element 19 comprises two Belleville springs in series. In this aspect, the Belleville springs are compressed approximately 0.008" nominally. Other examples of a biasing element include, but are not limited to, wave springs, elastomer washers, and alike. On the side opposite the retaining ring 21, the biasing element 19 is disposed adjacent to a ferrule 13. In one aspect, as axial force is applied, the biasing element 19 is biased between the retaining ring 21 and the ferrule 13. Suitable materials for the biasing element 19 include, but are not limited to, stainless steel, PEEK, coated steel, and alike.

Ferrule 13 lies within the nut cavity 15. In one aspect, the ferrule 13 is physically attached to the male element 5. This attachment can be accomplished by any method known to those skilled in the art, such as welding, resistance welding, electron beam welding, laser welding, brazing, and alike. The ferrule 13 is disposed adjacent to the biasing element 19 on its distal surface. In the resting position, i.e., in the absence of applied axial force, cavity space 27 separates the proximal surface of the ferrule 13 from an edge of nut housing 33. As axial force is applied, this cavity space 27 (continuous with cavity 15) becomes smaller as the edge of the nut housing 33 approaches the proximal surface (the surface disposed toward the conical tip 17 of the male element 5) of the ferrule 13. Suitable materials for the ferrule 13 include, but are not limited to, stainless steel, steel, and polymeric materials such as reinforced PPS or PEEK.

Figure 2A:
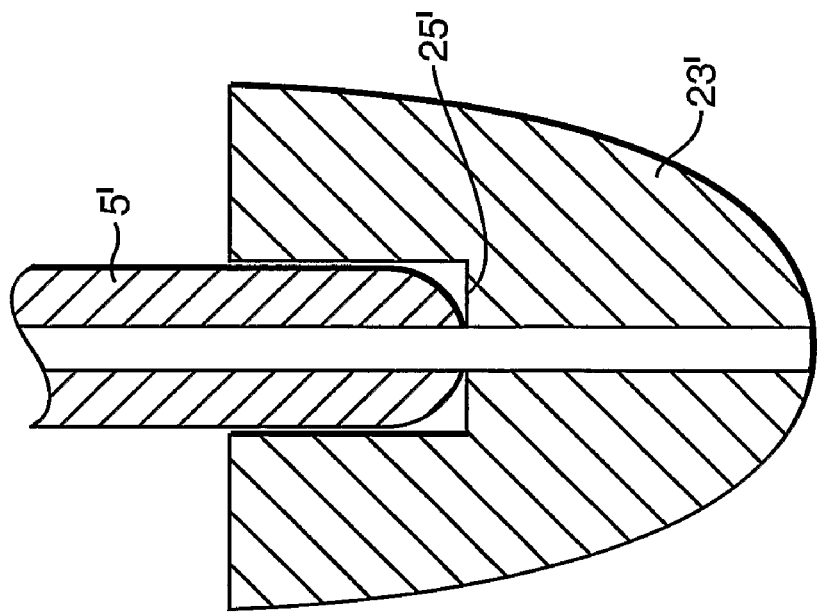
FIG. 2 depicts a side by side comparison of an embodiment of the present invention with a typical coupling system in the prior art.
Figure 2B:
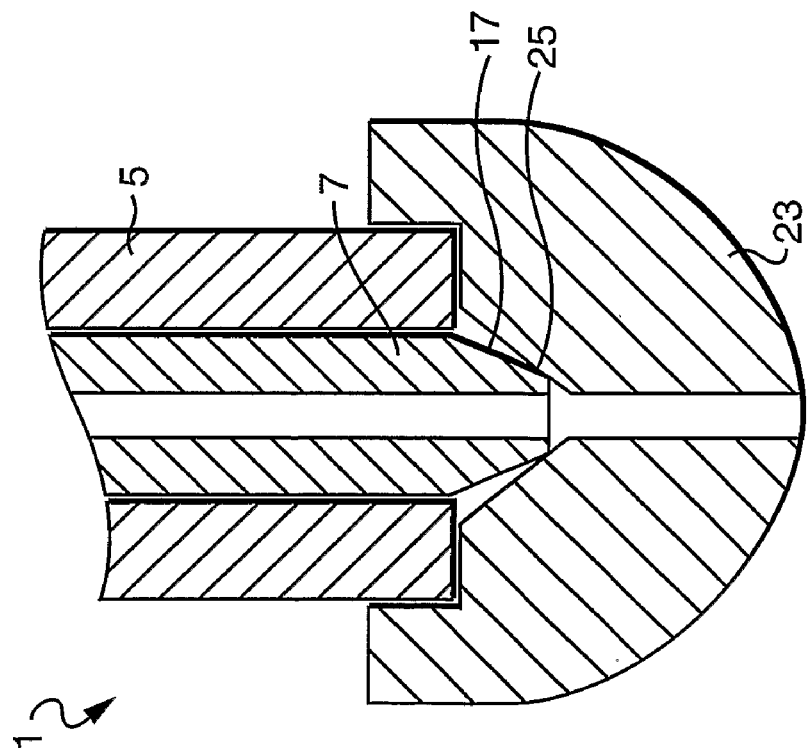

FIG. 2 compares the present invention (FIG. 2a) with a typical coupling system in the prior art (FIG. 2b). In particular, FIG. 2a depicts the mating between a coupling element 1 of the present invention and a female sealing element 23. The male sealing element 5 has a first end 7 whose apical surface 17 is defined by a conical geometry. The receiving element of the female sealing element 23, i.e., the receptacle 25, has a complementary conical geometry. This complementary design facilitates a fluid-tight seal between the male sealing element 5 and the female sealing element 23. This design also promotes centering of the male element 5 about the female element 23.

As axial compression is applied, the male element 5 is displaced toward the female element 23, in particular, the female receptacle 25. As the applied force is increased, the apical portion of the first end 7 of the male element 5 deforms (as indicated by the arrows in FIG. 2) providing a surface to surface seal between the male element 5 and female element 23.

A closer examination of the elements involved at the juncture of the seal reveals that there is a mismatch of angles between the conical apical surface 17 of the male element 5 and the receptacle 25 of the female element 23. See FIG. 3. In one aspect, this mismatched angle ranges from 1 to 2 degrees. This offset provides a functional advantage. As an axial force is applied to the male sealing element in the direction of the female sealing element 25, the offset of the conical apex of the male element 17 deforms and makes metal to meal contact with the female sealing element 25. By having this offset, contact forces are increased between the male element and female element making a fluid-tight seal.

Figure 3:
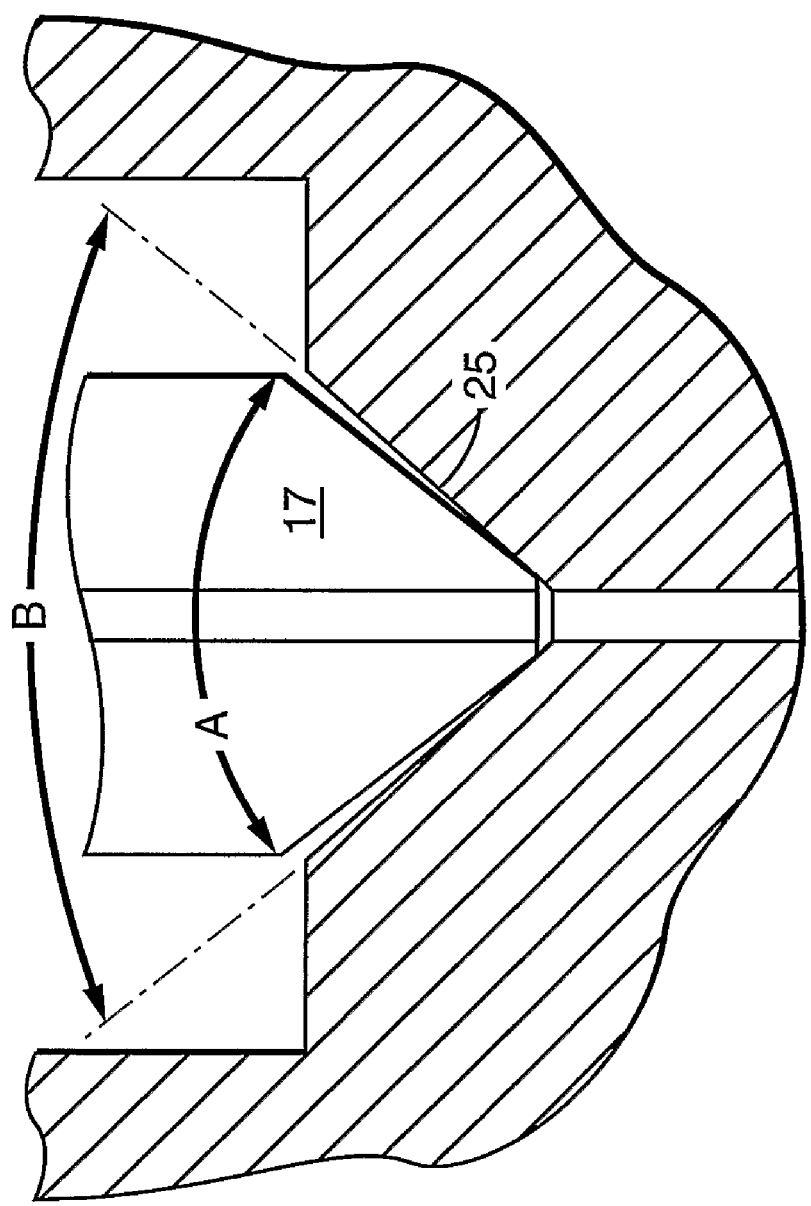
FIG. 3 depicts the mismatched angle formed between a male and female element of the present invention.

Returning to FIG. 2, the coupling system of the present invention (FIG. 2a) is contrasted with a typical coupling system of the prior art. As already described, the coupling system of the present invention comprises a male sealing element 5 interfacing with a female sealing element 23. The apical portion 17 of the first end 7 of the male element 5 is defined by a conical geometry. The female receptacle 25 receives the male element 5 and is defined by a complementary conical geometry. As depicted in FIG. 3, the angle of the male apical portion 17 and the female receptacle 25 are mismatched, thus facilitating greater contact between the male 5 and female 23 elements.

FIG. 2b depicts a typical coupling system found in the prior art. In this coupling system, there is a male element 5' that is received by a female element 23'. As axial force is applied to the male element 5', this element 5' is driven into a female receptacle 25' of the female element 23'. Deformation occurs at the apical portion of the male element 5'. However, as shown in FIG. 2b, the apical portion of the male element 5' is spherical, thus when compared with the present invention, less contact is made between the male 5' and female 23' elements. Additionally, there is no mismatch of angles between the male 5' and female 23' elements, thus even less contact forces are going to be operative. Further, due to the spherical geometry of the male element 5', centering of the male element 5' about the female 23' element is less likely as compared to the present invention. The coupling system depicted in FIG. 2b is not well suited to sealing under high pressure.

A method of forming a high pressure seal is disclosed herein. An axial compression force can be applied to the male sealing element of the present invention. This compression force will displace the male sealing element toward a female sealing element. In one aspect, the male sealing element has a first end which defines a conical sealing surface. In this aspect, the female sealing element defines a nearly complementary conical geometry. There is a mismatch angle between the male conical surface and the female sealing element in this aspect. Deformation of the male's first end conical surface occurs as the axial compression force is applied, thereby effectuating a fluid-tight seal.

As the axial force on the male element is applied, the apical portion of the first end deforms elastically in cooperation with the conical female receptacle in the female element. In order to increase the sealing, the axial force is increased thereby increasing both the seal pressure and the seal area. Additionally, the fact that the sealing surfaces are nearly matching cones enhances the coupling's ability to tolerate normal axial mis-alignments between seal members.

The male (cone) element pressed into the female receptacle will tend to be self-aligning. This will create a seal when the degree of mis-alignment (linear offset or angular offset) may have prevented sealing, or caused occluded flow with other coupling styles.

In order to assure a fluid-tight seal, the relative axial force should be in the range of between about 50 to about 65 lbs. Given the small surface area at the contact interface, the axial forces will concentrated there at creating a sealing pressure in range from about 40,000 to about 50,000 psi.

Some of the advantages to the present invention include, but are not limited to, an increase in seal pressure due to wedging of the male and female elements; an increase in seal area with increase in pressure; an ability to seek the center (auto-align) as the male element is inserted into the female receptacle, this alignment avoids occlusion of flow by mis-centered placement of the male and female elements; and an ability to accommodate non-aligned parts due to fabrication errors.

Although the invention has been described with respect to various embodiments, it should be realized this invention is also capable of a wide variety of further and other embodiments within the spirit and scope of the appended claims.

What is claimed is:

1. A coupling element, comprising:
   a male sealing element having a first end, second end, and a longitudinal axis extending between said first end and said second end, wherein said male sealing element has a generally cylindrical shape, wherein said male sealing element defines a fluid passageway therethrough for the transmission of fluid, wherein said male sealing element is slideably coupled to a ferrule, wherein said first end defines a conical sealing surface, wherein said conical sealing surface has a mismatched angle to a female sealing element, wherein said female sealing element defines a complementary conical geometry and said male conical surface extending beyond a proximal portion of said female element; and
   a biasing element disposed between a retaining ring and said ferrule located within a cavity in said female sealing element for biasing said first end into direct abutting contact with said female sealing element with a biasing force sufficient to form a fluid-tight seal between said first end and said female sealing element wherein said retaining ring assists in maintaining the integrity of said biasing element and said ferrule and said retaining ring provides a surface for said biasing element to be biased against when an axial force is applied.

2. The coupling element of claim 1, wherein said mismatched angle ranges from about 1 to about 2 degrees.

3. The coupling element of claim 1, wherein said male sealing element forms a metal to metal fluid-tight seal when mated with a female sealing element.

4. The coupling element of claim 3, wherein said male sealing element's first end deforms when mated with said female sealing element.

5. The coupling element of claim 3, wherein said male sealing element is centrally positioned when mated with said female sealing element.

6. The coupling element of claim 1, wherein said biasing element comprises a compression spring.

7. The coupling element of claim 6, wherein said compression spring is a Belleville spring.

8. The coupling element of claim 1, wherein said male sealing element comprises metal.

9. The coupling element of claim 8, wherein said metal is stainless steel.

10. A method for forming a fluid-tight, high pressure seal, comprising:

providing a male sealing element having a first end, second end, and a longitudinal axis extending between said first end and said second end, wherein said male sealing element has a generally cylindrical shape, wherein said male sealing element defines a fluid passageway therethrough for the transmission of fluid, wherein said male sealing element is slideably coupled to a ferrule, wherein said first end defines a conical sealing surface, wherein said conical sealing surface has a mismatched angle to a female sealing element, wherein said female sealing element defines a complementary conical geometry and said male conical surface extending beyond a proximal portion of said female sealing element, and providing a biasing element disposed between a retaining ring and said ferrule located within a cavity in said female sealing elment for biasing said first end into direct abutting contact with said female sealing element with a biasing force sufficient to form a fluid-tight seal between said first end and said female sealing element arranged such that said retaining ring assists in maintaining the integrity of said biasing element and said ferrule and said retaining ring provides a surface for said biasing element to be biased against when an axial force is applied; and applying a compression force in an axial direction of the male sealing element toward said female sealing element sufficient to form a fluid-tight, high pressure seal.

* * * * *